US008088056B2

(12) United States Patent
Gross et al.

(10) Patent No.: US 8,088,056 B2
(45) Date of Patent: Jan. 3, 2012

(54) THIN CALIFORNIUM-CONTAINING RADIOACTIVE SOURCE WIRES

(75) Inventors: Ian G Gross, Clinton, TN (US); Larry A Pierce, Kingston, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1172 days.

(21) Appl. No.: 11/379,824

(22) Filed: Apr. 24, 2006

(65) Prior Publication Data

US 2006/0195003 A1 Aug. 31, 2006

Related U.S. Application Data

(62) Division of application No. 10/941,131, filed on Sep. 15, 2004, now Pat. No. 7,093,476.

(51) Int. Cl.
*A61N 5/00* (2006.01)

(52) U.S. Cl. .......... 600/3

(58) Field of Classification Search .......... 600/1–4, 600/7, 8; 72/402, 76
See application file for complete search history.

(56) References Cited

U.S. PATENT DOCUMENTS

| | | | | |
|---|---|---|---|---|
| 5,141,487 | A | 8/1992 | Liprie | |
| 5,282,781 | A | 2/1994 | Liprie | |
| 5,755,695 | A | 5/1998 | Erickson et al. | |
| 6,217,503 | B1 * | 4/2001 | Weinberger et al. | 600/3 |
| 6,352,500 | B1 | 3/2002 | Halpern | |
| 6,817,995 | B1 * | 11/2004 | Halpern | 604/524 |
| 2002/0055666 | A1 * | 5/2002 | Hunter et al. | 600/1 |
| 2002/0058852 | A1 * | 5/2002 | Halpern et al. | 600/3 |
| 2003/0204126 | A1 * | 10/2003 | Rivard | 600/3 |

FOREIGN PATENT DOCUMENTS

| | | |
|---|---|---|
| DE | 93 04 905.6 | 8/1993 |
| DE | 10341716 | 10/2004 |
| EP | 1 555 331 | 7/2005 |
| GB | 1053960 | 1/1967 |
| GB | 1186379 | 4/1970 |

OTHER PUBLICATIONS

Rivard, M. J., Wierzbicki, J.G., Van den Heuvel, F. "Clinical brachytherapy with neutron emitting 252Cf sources and adherence to AAPM TG043 dosimetry protocol," Jan. 1999, Med. Phys. (1), pp. 94-95.*

Martin, R.C., Halpern, D.S. "Development of Minature High-Dose-Rate 252Cf Sources for Boron-Enhanced and Fast Neutron Brachytherapy," 2002, Oak Ridge National Laboratory, Oak Ridge, TN, pp. 1-2.*

Written Opinion WO0043066, "Tip Configuration for Radiation Source Wires," Jul. 27, 2000.

* cited by examiner

*Primary Examiner* — Charles A Marmor, II
*Assistant Examiner* — Christine Hopkins
(74) *Attorney, Agent, or Firm* — Joseph A. Marasco

(57) ABSTRACT

A cermet wire includes at least 1% californium-252 and is characterized by a diameter of no more than 0.0225 inch.

1 Claim, 1 Drawing Sheet

THIN CALIFORNIUM-CONTAINING RADIOACTIVE SOURCE WIRES

CROSS-REFERENCE TO RELATED APPLICATIONS

This application is a divisional application of U.S. patent application Ser. No. 10/941,131 filed on Sep. 15, 2004 now U.S. Pat. No. 7,093,476, entitled "Method For Fabricating Thin Californium-Containing Radioactive Source Wires", the entire disclosure of which is incorporated herein by reference.

STATEMENT REGARDING FEDERALLY SPONSORED RESEARCH

The United States Government has rights in this invention pursuant to contract no. DE-AC05-00OR22725 between the United States Department of Energy and UT-Battelle, LLC.

BACKGROUND OF THE INVENTION

The invention relates to the fabrication of wires containing radioactive californium-252. In particular, thinner radioactive wires having a more nearly circular cross section are achieved through a series of pressurization steps using a collet fixture used as a wire shaping apparatus.

Brachytherapy is a method of treating cancer in which a radioactive source is positioned within the body at the site of the tumor. Neutron brachytherapy using californium-252 (Cf-252) radioactive sources has been practiced for 30 years, typically using either low dose rate (LDR) treatments or, for some tumors, high dose rate (HDR) therapy. HDR therapy is preferred because of its shorter treatment times. However, to date, only relatively large (approximately 3-mm outer diameter) sources contain sufficient Cf-252 mass to provide neutron intensities in the HDR range. The present HDR sources are too large to be used for interstitial (intraorgan) treatments, but are ideal for intracavitary treatments (gynecological, rectal, head, neck, and oral cavity treatments, etc.). As a result, interstitial treatments have been limited to the LDR regime.

High specific activity (HSA) Cf-252 source material has not previously been available in a form thin enough for use in smaller sources of appropriate sizes for interstitial treatments (e.g., brain, prostate, breast, lung, etc.). The present invention seeks to overcome this limitation by providing thinner high specific activity Cf-252 source material.

Oak Ridge National Laboratory (ORNL) is the only production source for Cf-252 in the United States. One other production center is in Russia. Both sites manufacture Cf-252 medical sources. Russia's Cf-252 source forms do not have a specific activity as high as that available from the Cf-252 cermet wire forms available from ORNL.

The fabrication of very thin gamma or photon-emitting source wires for use in brachytherapy sources is typically not as difficult as that of Cf-containing cermet wire. Conventional gamma sources have a great advantage in that very thin wires can first be fabricated with non-radioactive material, and then placed inside the core of a nuclear reactor where they are activated to the desired radioactivity. Segments of these activated wires are then sealed as radioactive sources and used as is. The use of iridium-192 wires as small as 0.0134" in brachytherapy sources has been reported.

Unfortunately, the man-made element californium cannot be handled outside of heavily shielded containments such as hot cells. Californium-252 is obtained through a wet chemical process of dissolutions, purifications, precipitations, and wire fabrication inside a heavily shielded and highly contaminated hot cell. All operations must be performed remotely, and hands-on operations with the resultant cermet wires are not possible due to intense neutron emission. The nature of cermet wire, as a metallic matrix with ceramic impurities (californium oxide), makes miniaturization increasingly difficult in the production of a structurally sound wire, especially a heavily loaded (>1% by weight Cf-252) cermet wire.

ORNL's cermet wires contain californium oxide blended within a palladium metal matrix. The ceramic oxide acts as an impurity within the palladium, and degrades Pd workability as the oxide concentration increases above 1% by weight. The wires are formed by rolling a previously melted cermet pellet through smaller and smaller grooves of a jeweler's rolling mill. The rolling mill currently used within the Californium Facility hot cells can produce a wire with measurable dimensions approaching 0.75 mm. However, the effective diameter is closer to 1 mm due to its trapezoidal cross-section.

An example of prior technology is D. S. Erickson and A. Feiring, "Guidewire Steering Handle and Method of Using Same", U.S. Pat. No. 5,755,695, Issued May 26, 1998.

BRIEF SUMMARY OF THE INVENTION

It is a first object of the invention to provide a miniaturized Californium-252 cermet wire.

It is another object of the invention to produce a round cylindrical wire as compared to the current trapezoid-shaped wire.

It is another object of the invention to provide a straight wire segment to simplify the cutting process and prevent breakage during processing.

In accordance with one aspect of the present invention, the foregoing and other objects are achieved by a cermet wire that includes at least 1% californium-252 and is characterized by a diameter of no more than 0.0225 inch.

Figure 1:
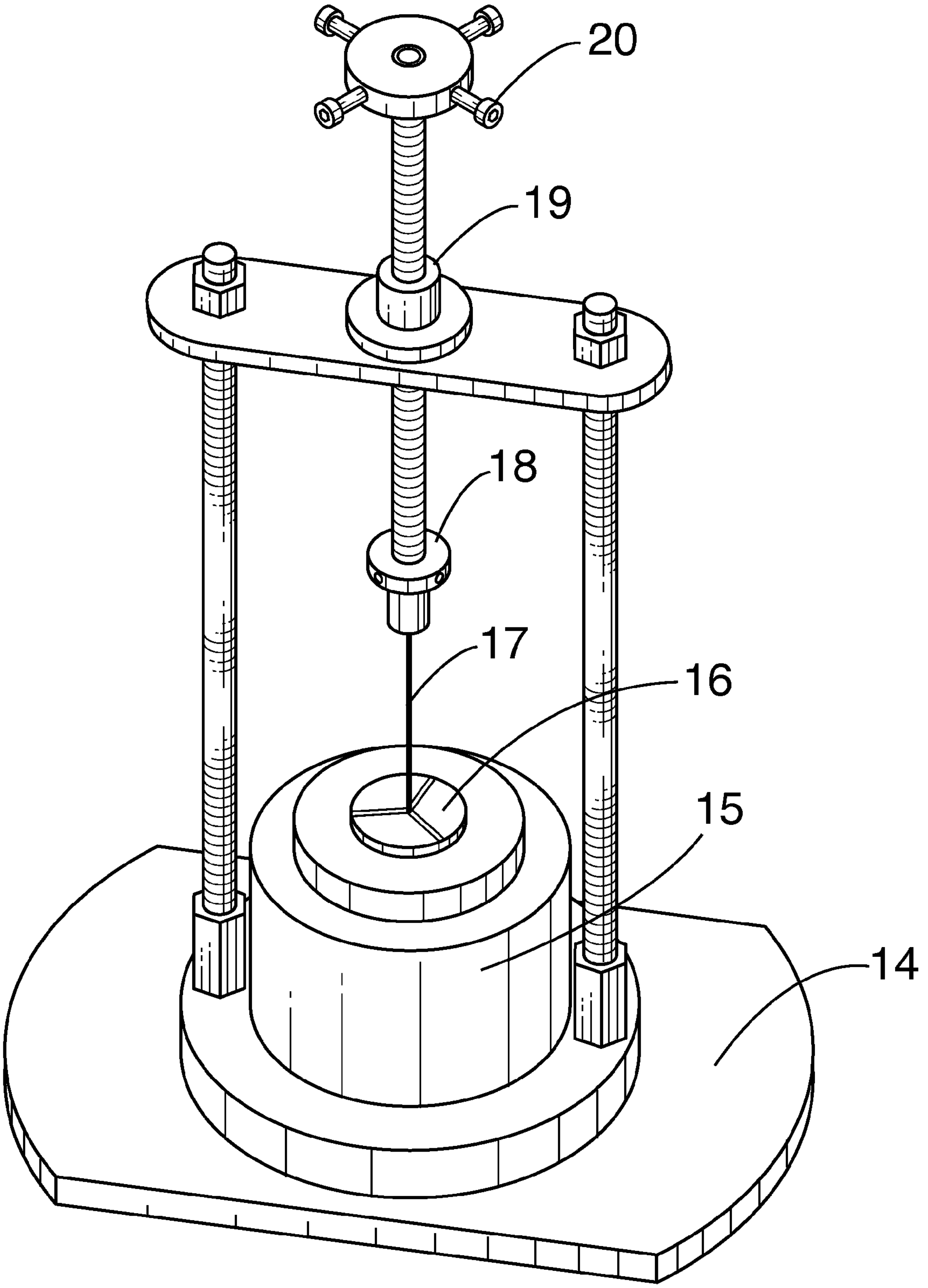
FIG. 1 is a perspective view of a wire shaper apparatus in accordance with the invention.

For a better understanding of the present invention, together with other and further objects, advantages and capabilities thereof, reference is made to the following disclosure and appended claims in connection with the above-described drawings.

DETAILED DESCRIPTION OF THE INVENTION

We have developed an effective method for significantly reducing the cross section of ORNL's heavily loaded (>1% by weight Cf-252) cermet wires. Of particular advantage is that our method is well suited for use in hot cells where the high-intensity, miniature Cf-252 sources are produced.

The invention is a wire shaping apparatus and method in which pneumatically activated collet jaws are used to apply controlled pressure to the circumference of a radioactive cermet brachytherapy source wire. A commercial pneumatically operated collet fixture is employed as a wire "shaper" apparatus. By repeatedly working the length of the wire through the collet fixture at sequentially increasing pressure, much thinner wires are produced than could previously be achieved.

In the drawing, a commercial collet fixture 15 having pneumatically activated jaws 16 was mounted on a base 14 for manual operation using a pneumatic switch (not shown). Air pressure activates the collet jaws, or fingers, which compress a portion of the cermet wire 17. After the wire is compressed, the air pressure is turned off, causing the collet jaws to release the wire. Two collets with different jaw size openings were used to sequentially process the wire. One collet reduced the diameter of the wire obtained from the conventional rolling mill, and the second collet further shrank the wire to the target diameter.

Just as important, the method also substantially improves the wire cross section to a more nearly circular shape, making it much better adapted for handling in the subsequent fabrication process. Specifically, the method eliminates the use of a diamond or trapezoidal cross-sectional-shaped wire that had been produced with the best previous method. In our process, the shaped wire, up to a few inches in length, is cut into short segments in a cutter fixture. Each segment is then placed within a medical source capsule. The new wire shaping method is sufficiently simple that it is ideally suited for use in the hot cell brachytherapy source capsule fabrication process.

Referring again to the drawing, a wire holder 18 is mounted above the collet fixture 15. The wire holder 18 is used to advance the wire 17 manually through the shaper using a screw mechanism 19 controlled by a handle 20. The wire holder 18 is used to both grasp and position the wire 17 relative to the collet fixture 15. Each pressurization pulse causes the collet jaws to compress the wire over a length of <⅛ inch, so the wire must be advanced a short distance through the collet between pulses. In addition, the wire is inverted in the holder each pass to ensure both ends are shaped, and that the wire is uniform in diameter over its entire length. The handle is rotated a fraction of a turn between pulses, and in time the entire wire is advanced through the shaper at each pressure setting. The process is repeated using a series of increasing air pressure settings until the wire diameter has been reduced to the desired size.

An initial pressure setting of 40 psi was used to shape the wire. After completing wire shaping at 40 psi, the pressure was increased by 10 to 20 psi, and another wire pass through the shaper was completed. The pressure continued to be increased until the target wire diameter with uniform cross section was obtained. This was determined by passage of the wire through a go/no-go gauge of the target diameter. The wire shaping steps typically used a 40 to 60 psi range of pressures, although a maximum of 90 psi was available for use. The wire required periodic annealing at high temperature to mitigate shaping-induced work hardening of the wire; i.e., to reduce the wire's resistance to further shaping as the diameter decreased. More frequent annealing was required at smaller wire diameters.

In practice, the thinnest wire available from the conventional rolling mill was used as the feed material for the wire shaper. Although nominally ~0.75 cm in diameter, these wires would not pass through a go/no-go gauge of that diameter. This wire was processed through the wire shaper, and the process repeated until the target wire diameter of 0.0225 inch (0.572 mm) was achieved. Confirmation was provided by the go/no-go gauge. In principle, even thinner wires could be achieved with continued shaping through another, narrower collet. In laboratory demonstrations using a manganese-copper alloy wire as a surrogate for the cermet wire, wire thicknesses as small as 0.017 inch (0.43 mm) were demonstrated.

Collets with smaller jaw openings can be used to provide even thinner wires, below the demonstrated production thickness of 0.0225 inch (0.57 mm) Cf-containing wires and laboratory demonstration of 0.017 inch (0.43 mm) surrogate wires. The practical minimum wire thickness using this approach has not been determined, but should be less than 0.4 mm.

Compared to other methods of wire fabrication such as rolling mills, swaging and drawing, we have produced significantly smaller californium cermet wires than previously fabricated. Our method is operationally simpler and has a simpler hardware design than other options for producing thinner wires. The method has a lower probability of catastrophic wire damage (e.g., wire not going straight through the rolling mill groove, and being squashed between grooves). This method is gentler than swaging, and therefore less likely to splinter the wire as a result of internal defects inherent in the cermet structure with heavily loaded Cf oxide. This reflects the high revolutions per minute (RPM) during swaging vs. negligible RPM with our manually operated method. Pneumatic operation of our shaper provides more reliable long-term operation within a hot cell environment than, for example, electrical motors. Unlike swaging, the method promises reliable in-cell operation with little or no maintenance or adjustment. The method also provides higher specific activities than other source forms currently available that can be configured as thin sources. During a production run, our cermet product can be cut into multiple source segments of comparable specific activities for fabrication of closely matched sources.

The shaping process can be motorized such that the pneumatic switch and the wire advancement mechanism, currently operated manually, can be synchronized to work automatically throughout each pass of the cermet wire through the shaper.

A small heating collar or heat lamp can be used to anneal the wire as it advances through the shaper. By this means, the wire need not be removed from the shaper apparatus and placed in a furnace for periodic annealing.

This technology was specifically designed to be used for the treatment of cancer via the brachytherapy method, its primary application. However, the same technology could be used whenever a very thin or very compact neutron source is required. One example would be as a line source or point source for purposes of instrument calibration or for specialized physics experiments.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A cermet wire comprising at least 1 wt % californium-252, said cermet wire being characterized by a diameter of no more than 0.0225 inch and an essentially circular cross-section.

* * * * *